Nov. 6, 1973
H. K. GORTZ
Plant Pat. 3,404
CHRYSANTHEMUM PLANT
Filed Aug. 11, 1971
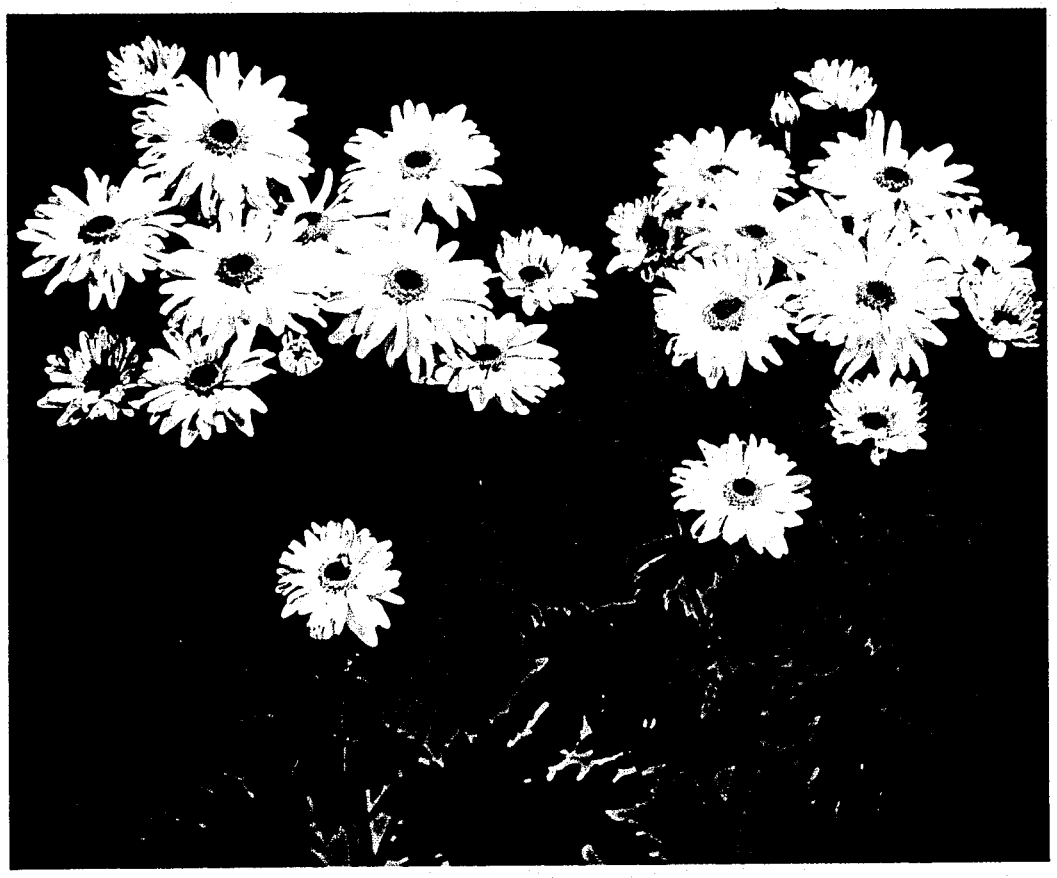

United States Patent Office

Plant Pat. 3,404

Patented Nov. 6, 1973

3,404

CHRYSANTHEMUM PLANT

Helmut Karl Gortz, Cagliari, Sardinia, Italy, assignor to Yoder Brothers, Inc., Barberton, Ohio Filed Aug. 11, 1971, Ser. No. 170,936

Int. Cl. A01h *5/00*

U.S. Cl. Plt.—74 1 Claim

The present invention comprises a new and distinct cultivar of a daisy form chrysanthemum plant which is a sport of the cultivar known in the United States as Yellow Bonnie Jean.

The new cultivar is similar in many respects to Yellow Bonnie Jean having the same characteristics of:

(1) Flower size and form.
(2) Foliage size, shape and color.
(3) Flowering response.

The new cultivar is distinguished from the parent Yellow Bonnie Jean by the following characteristics:
(1) 2″ more vigor than parent.

observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from April through mid-November when grown as a pot mum and May through mid-November when grown as a pompon; in the West Coast, South and Southwest, April through November for both pompons and pot mums.

The accompanying drawing shows the unique characteristics of the new cultivar, the color being as nearly true as possible with color illustrations of this type. Improved Yellow Bonnie Jean is shown on the left and Yellow Bonnie Jean is shown on the right.

In the description which follows, color deferences are made to the Munsell Color Book, 1963 edition, and comparisons are made with the cultivar Yellow Bonnie Jean. Where only a single designation or value appears for the new cultivar, the same applies to the parent cultivar.

Botanical classification: *Chrysanthemum morifolium*

| | Improved Yellow Bonnie Jean | Yellow Bonnie Jean |
|---|---|---|
| Bloom: | | |
| Size | 3″ | |
| Fully expanded | 3½″ | |
| Borne | Clusters on elongated pedicels | |
| Stems | Short and strong | |
| Form | Daisy | |
| Permanence | 10 days | 7 days. |
| Color (Munsell): | | |
| Center of flower | Light green, 2.5GY6/8 to light yellow green, 10Y8.5/10 | Yellow, 7.5Y8.5/8 to light yellow, 7.5Y9/4. |
| Base of petals | Yellow, 7.5Y8.5/10 to yellow, 7.5Y8.5/8 | Do. |
| Inside of petals | do | Light yellow, 7.5Y9/4 to very pale yellow, 7.5Y9/2. |
| Reverse of petals | Light yellow, 7.5Y9/6 to light yellow, 7.5Y9/4 | Light yellow. |
| Tonality from a distance | Yellow | Light yellow 7.5Y9/4. |
| Discoloration | Yellow, 7.5Y8.5/8 | |
| Petals: | | |
| Texture | Smooth | |
| Appearance and form | Open at base, broaden quickly slightly longitudinal roll, broad shallow keel, tapering to a blunt point. | |
| Arrangement | Composite, whorled on a single receptacle | |
| Persistence | Resist shatter | |
| Fragrance | Typical chrysanthemum | |
| Reproductive organs: | | |
| Stamen, anthers | 150 to 200 | |
| Pollen | None to abundant (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 34″–38″ grown as a single stem cut flower, given 3 to 4 long day weeks and a total crop time of 13–14 weeks during the various seasons of the year as defined in the time-tables published by Yoder Brothers, Inc.; approximately 18″–20″ when grown as a pinched pot mum grown as a spray pot and given 10 week tall treatment timing. | Approximately 32″–36″ grown as a single stem cut flower, given 3–4 long day weeks and a total crop time of 13–14 weeks during the various seasons of the year as defined in the time-tables published by Yoder Brothers, Inc.; approximately 16″–18″ when grown as a pinched pot mum grown as a spray pot and given 10 week tall treatment timing. |
| Spread | None when grown single stem to 10″ as a pot | |
| Foliage: | | |
| Top side | Green, 7.5GY3/4 | |
| Size | 6″ long, 4″ wide | |
| Quantity | Numerous | |
| Shape | Spatulate lobed | |
| Texture | Coarse | |
| Ribs and veins | Very prominent | |
| Edge | Deeply indented | |
| Serration | Moderate | |
| Underside | Light green, 7.5GY5/4 | |
| Stipules | Prominent | |

(2) A darker yellow flower color.
(3) Far less oxidation or fading of the yellow pigmentation in the petals under high temperature and high light conditions.

The new cultivar was discovered at Horsens, Denmark, and was asexually reproduced at Cagliari, Sardinia, Italy, by cuttings, and has been found to retain its distinctive characteristics through successive propagations.

The new cultivar when grown in the vicinity of Barberton, Ohio, has a response period of approximately 10 weeks, and the following detailed description is based on

I claim:

1. A new and distinct cultivar of daisy form chrysanthemum characterized particularly to the uniqueness when compared to the parent cultivar Yellow Bonnie Jean by its darker yellow flower, color, its 2″ more vigor, and far less oxidation or fading of the yellow pigmentation of the petals under high light, high temperature conditions.

No references cited.

ROBERT E. BAGWILL, Primary Examiner